United States Patent [19]

Reid

[11] Patent Number: 5,366,990
[45] Date of Patent: Nov. 22, 1994

[54] METHOD FOR TREATING ALCOHOL ABUSE AND ALCOHOLISM

[76] Inventor: Larry D. Reid, 65 23rd St., Troy, N.Y. 12180

[21] Appl. No.: 792,237

[22] Filed: Nov. 14, 1991

[51] Int. Cl.$^5$ .......................................... A61K 31/415
[52] U.S. Cl. .................................... 514/397; 514/811
[58] Field of Search ............................... 514/402, 397

[56] References Cited

U.S. PATENT DOCUMENTS

| | | |
|---|---|---|
| 4,133,348 | 3/1979 | Pystnitskaya . |
| 4,144,348 | 3/1979 | Pyatnitskaya et al. ............... 424/274 |
| 4,761,429 | 8/1988 | Blum . |
| 4,808,574 | 2/1989 | Brekhman . |
| 4,895,848 | 1/1990 | Traber . |
| 4,931,277 | 6/1990 | Fontaine . |
| 4,968,692 | 11/1990 | Linnoila et al. ....................... 514/811 |
| 4,983,632 | 1/1991 | Gessa . |
| 5,013,752 | 5/1991 | Dobbins . |
| 5,109,007 | 4/1992 | Linnoila et al. ....................... 514/811 |

OTHER PUBLICATIONS

Lister, R. G. et al., Life Sci 44(2):111–9 (1989) Abstract.
Durcan, M. J. et al., J. Pharmacol Exp Ther 258(2):576–82 (1991) Abstract.
Krylov, S. S., Ann 1st Super Sanita (14)1:77–80 (1978) Abstract.
"Attenuation of the Effects of Ethanol on Social Behavior by Alpha$_2$-Adrenoceptor Antagonists", Durcan, Michael J., Dec. 14, 1988.
"Interactions of Alpha$_2$-Adrenoceptor Antagonists with Medetomidine and with Ethanol in a Holeboard Test", Durcan, M. J. Aug. 20, 1988.
"Antagonism of Ethanol Intoxication in Rats by Inhibitors of Phenylethanolamine N-Methyltransferase", Mefford, Ivan N. Jan./Feb. 1990.
"Behavioral Effects of Alpha$_2$ Adrenoceptor Antagonists and Their Interactions with Ethanol in Tests of Locomotion, Exploration, and Anxiety in Mice", Durcan, Michael J., Springer-Verlag 1989.
"Norepinephine Turnover and Voluntary Consumption of Ehtnaol in the Rat", Socaransky, S. M., 1985.
"Attenuation of Ethanol Intoxication by Alpha$_2$ Adrenoceptor Antagonists", Lister, Richard G., Nov. 15, 1988.
"Behavioral Effects of the Inhibitors of Phenylethanolamine-N-methyltransferase, LY 78335 and LY 134046, and Their Interactions With Ethanol", Durcan, Michael J., Nov. 27, 1989.
"Effects of $\alpha_2$-Adrenergic Drugs on the Alcohol Consumption of Alcohol-Preferring Rats", Korpi, E. R., Nov. 22, 1989.

*Primary Examiner*—S. J. Friedman
*Assistant Examiner*—William Jarvis
*Attorney, Agent, or Firm*—Christopher E. Blank; James Sullivan

[57] ABSTRACT

A method for decreasing appetite for alcohol in humans which comprises the steps of providing an effective dosage of an alpha-2-adrenergic antagonist to the subject.

12 Claims, 9 Drawing Sheets

METHOD FOR TREATING ALCOHOL ABUSE AND ALCOHOLISM

BACKGROUND

Alcohol abuse and alcoholism and their consequences are considered by many Nations to be their most serious health problem. Proven methods for treating and preventing alcohol abuse and alcoholism have not been found to date. Any treatment method which ameliorated the effects of alcohol abuse and/or alcoholism would be beneficial.

Attempts have been made to develop pharmaceutical agents to treat alcohol abuse and alcoholism. For instance, the approach of using an agent which would cause nausea upon the event of alcohol consumption has been discussed and attempted. These agents, however, have not been shown to be clinically effective in well-controlled clinical trials.

Another approach has been premised on the notion that alcohol abuse and alcoholism are manifestations of anxiety and/or depression and have attempted to treat alcohol abuse or alcoholism with pharmocotherapies used in treating severe anxiety and/or depression. Generally, these treatments, and particularly antianxiety medications, have not been found to be clinically effective in well-controlled clinical trials.

Another approach is premised on the notion that specific pharmaceutical agents might modify the motivation for drinking alcohol. In effect, this approach requires a pharmaceutical agent which changes the patient's appetite for alcoholic beverages. This allows for the possibility that a subject's propensity to drink excessively can be modified even during the course of drinking. By decreasing motivation to drink, such agents would be particularly helpful in preventing relapse back into periods of excessive drinking following a period of abstinence. This approach is consistent with the observations that alcohol abuse and alcoholism tends to run in natural families (this has lead to the suggestion that alcoholism might involve specific, inheritable, neurochemistries). If this is the case, then, pharmaceutical agents may be able to effectively alter this specific neurochemistry in order to decrease the propensity to take excessive amounts of alcoholic beverages which is the essence of alcohol addictive behavior. There are events in the history of an individual that may also lead to states that might be similar to those that are characteristic of persons who inherit a risk for alcoholism. It follows that pharmaceutical agents will be useful in a variety of circumstances where the salient problem is propensity to drink alcoholic beverages extensively.

The idea that a pharmaceutical agent might be an effective therapy for alcohol abuse and alcoholism is supported by a number of recent observations. Maltrexone, for example, is an agent that reduces laboratory animal's drinking of alcoholic beverages and has recently been shown to be an effective pharmaceutical adjunct to other treatments for alcohol abuse and alcoholism. The modification of certain physiological processes, such as those associated with the renin-angiotensin system, have been shown, as another example, to modify the propensity to consume alcohol in laboratory rats. The accumulated data indicate that drugs might be useful in treating alcoholism and, further, that testing with laboratory animals is a useful means for determining what pharmaceutical agents may be useful as treatments for, or as adjuncts to other treatments for, alcohol abuse and alcoholism. Tests with animals predict what agents will be useful and will not be useful in changing or lowering the consumption of alcoholic beverages in people.

Alcohol abuse and alcoholism have been variously labelled. Some modern usage, for example, calls alcoholism alcohol dependence. What is characteristic, however, of all the conditions for which we seek better treatments is that they are characterized by excessive intake of alcoholic beverages over an extended period of time.

The inventor has found that a class of pharmaceutical agents effectively modifies the propensity of laboratory animals to consume alcohol and, therefore, constitutes a class of agents which have utility as treatments for alcohol abuse, alcoholism and/or alcohol dependence and similar conditions manifest as extensive, problematic use of alcoholic beverages. These agents are the alpha-2 adrenergic antagonists (often called alpha-2 adrenoceptor antagonists or simply alpha-2 antagonists).

SUMMARY OF THE INVENTION

Figure 1A:
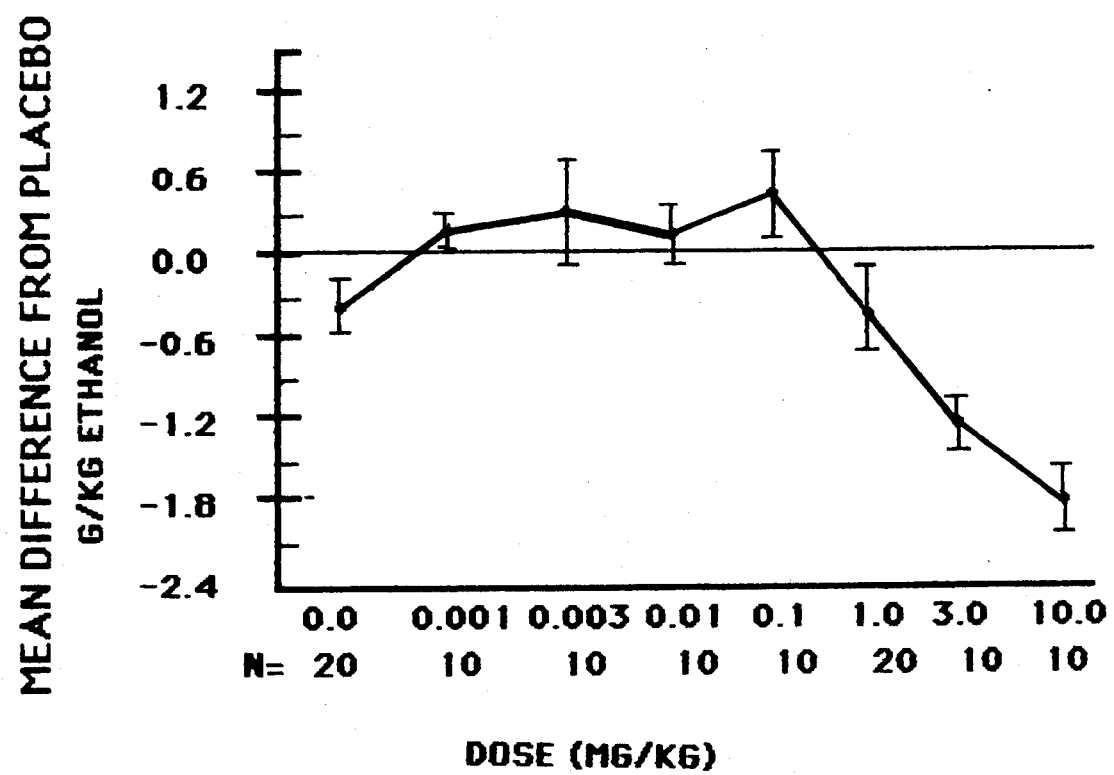
FIGS. 1A-1C and 2A-2C are graphs which summarize the effects of various doses of two alpha-2 adrenergic antagonists on rats' intakes of alcoholic beverage, in terms of grams of pure ethanol per kilogram of bodyweight (g/kg), grams of intake of water, and preference ratios (grams of alcoholic beverage divided by total fluid intake) during two hours. The data in the left column are for yohimbine. Data in right column are for methoxyidazoxan. The lines extending from data points are standard errors of the means.

The present invention relates to a novel method for decreasing the propensity of individuals to consume alcohol and alcoholic beverages. This novel method comprises the steps of providing an effective amount of an alpha-2 adrenergic antagonist agent to the subject to decrease the subjects' propensity to consume alcohol as alcoholic beverages. The specific method of providing the alpha-2 adrenergic antagonists to the subject is not critical to the invention. So, any effective means for delivering such agents can be employed, such as subcutaneous injection, intraperitoneal injection, or orally. Those skilled in the art of pharmacists will know individual alpha-2 adrenergic antagonist may be delivered to human subjects by a variety of techniques.

DETAILED DESCRIPTION OF THE INVENTION

The present invention is related to a novel method of treating alcohol abuse and/or alcoholism by providing effective doses of alpha-2 adrenergic antagonists to subjects exhibiting such addictive behaviors to reduce the subjects' propensity to consume alcohol and alcoholic beverages, either entirely or excessively.

Alpha-2 adrenergic antagonists include the pharmaceutical agents as yohimbine, idasoxane, piperoxane, midaglisole, fluparoxan, methoxyidazoxan, rauwolscine, efaroxan and imiloxan. Specifically, these agents are agents that act at a subclass of adrenergic receptors. Adrenergic receptors are those specialized places where hormones and neurotransmitters called catecholamines produce their specific effects. Adrenergic receptors have specifically been divided into two classes, alpha and beta receptors. Further, the class of alpha receptors has been divided into two classes, alpha-1 and alpha-2 receptors. The alpha-2 receptors have been characterized by bioassays and pharmacologically by binding assays. Recently, the alpha-2 receptors have been closed and specifically characterized. There are subtypes of alpha-2 receptors. The agents that will be useful in treating alcohol abuse and alcoholism may act at all or some of the alpha-2 receptor subtypes, since the agents used to discover their utility are both relatively specific for alpha-2 receptors and not specific for any one subtype of receptor. Further, it is only alpha-2 adrenoceptor antagonists (not agonists) that are useful in treating disorders associated with drinking alcoholic beverages.

Alpha-2 adrenergic antagonists have been used as therapeutic agents as antidepressants in treatment of diabetes and in inhibiting blood platelet aggregation. The invention discloses a new utility for this class of compounds which is not suggested in the art. As can be appreciated, alpha-2 adrenergic antagonists have been incorporated into pharmaceutical compositions which aid in the delivery of the active agent. As such, those skilled in the art will know several forms in which these agents may be used in the treatment of alcohol abuse and/or alcoholism. For instance, the invention also provides a pharmaceutical composition comprising alpha-2 adrenergic antagonist agents or a pharmaceutically acceptable salt in association with a pharmaceutically acceptable carrier. Any suitable carrier known in the art can be used to prepare this pharmaceutical composition. In such a composition, the carrier is generally a solid or liquid or a mixture of a solid and a liquid.

Solid form compositions include powders, granules, tablets, capsules (e.g., hard and soft gelatin capsules), suppositories, and pessaries. A solid carrier can be, for example, one or more substances which may also act as flavoring agents, lubricants, solubilizers, suspending agents, fillers, glidants, compressin aides, binders or tablet-disintegrating agents; it can also be an encapsulating material.

In powders, the carrier is a finely divided active ingredient. In tablets, the active ingredient is mixed with a carrier having the necessary compression properties in suitable proportions and compacted in the shape and size desired. The powders and tablets preferably contain up to 99%, e.g., from 0.03 to 99%, this range will obviously depend upon the activity of the alpha-2 adrenergic antagonist used.

Solid carriers include, for example, calcium phosphate, magnesium stearate, talc, sugars, lactose, dextrin, starch, gelatin, cellulose, methl cellulose, sodium carboxymethyl cellulose, polyvinylpyrrolidine, low melting waxes and ion-exchange resins.

The term "composition" is intended to include the formulation of an alpha-2 adrenergic antagonist with encapsulating material as carrier to give a capsule in which the antagonist (with or without other carriers) is surrounded by the carrier, which is thus in association with it. Similarly, cathets are included.

Liquid form compositions include, for example, solutions, suspensions, emulsions, syrups, elixirs, and pressurized compositions. The antagonist can be dissolved or suspended in a pharmaceutically acceptable liquid carrier such as water, an organic solvent, a mixture of both, or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g., cellulose derivatives, preferably sodium carboxymethyl cellulose solution), alcohols (including monohydric alcohols and polyhydric alcohols, e.g., glycerol and glycols) and their derivatives, and oils (e.g., fractionated coconut oil and arachis oil). For parenteral administration, the carrier can also be an oily ester such as ethyl oleate and isopropyl nyristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. When the antagonist is orally active it can be administered orally either in liquid or solid composition form.

The dosage required to curb alcohol consumption will vary from one alpha adrenergic antagonist to another. Optimal dosage will be determined by means similar to the method disclosed herein.

EXAMPLES

Examples of the kind of observations leading to the conclusion that alpha-2 adrenoceptor antagonists are effective medicines for treating alcohol abuse and alcoholism are described below.

Each of the experiments used methods that were devised to assess the potential efficacy of drugs as medicines for alcohol abuse and alcoholism used rats as experimental subjects. In other words, these specific procedures (developed by us) are a screen for selecting drugs that might reduce peoples' propensity to take large, excessive amounts of alcoholic beverages and, hence, a screen for pharmacological treatments for alcohol abuse and alcoholism. These procedures are, however, similar to those used by others to study alcoholism.

The idea that pharmacological interventions can be devised that will curb the propensity (motivation) to take alcoholic beverages is novel, except for drugs that merely make individuals sick when they ingest alcohol. Consequently, there is not a great deal of information concerning the predictive value of these kinds of tests in selecting agents to use with people. What data are available, however, strongly indicates that the conclusions derivable from these kinds of tests predict very well which drugs will be effective with alcoholics.

For instance, these kinds of tests have predicted that the opioid antagonist naltrexone would be effective with people and initial results from the clinic indicate that it is effective (see material in *Opioids, Bulimia, and Alcohol Abuse and Alcoholism*, Springer-Verlag, New York, 1990, Reid [ed.]). These kinds of tests have predicted that two agents (an ACE inhibitor and buspirone) that theoretically seemed promising did not, in fact, produce the desired effects with alcoholics (see material in *Novel Pharmacological Interventions for Alcoholism*, Springer-Verlag, New York, 1991, Naranjo and Sellers [ed.]). These kinds of tests predicted the small, but statistically significant, beneficial effects that are seen with people who drink excessively when they are administered serotonin reuptake inhibitors (e.g., fluoxetine), i.e., small, statistically significant effects are seen with both rats and people (e.g., *Novel Pharmacological Interventions for Alcoholism*, Springer-Verlag, New York, 1991, Naranjo and Sellers [ed.]). These tests predicted a less than desirable effect associated with the administration of methadone as a treatment for heroin addiction, i.e., certain doses of methadone actually increased drinking among both rats and people. Given that these are available data from both assessments with rats and double-blind, placebo-control studies with alcoholics, the conclusions derived from these kinds of tests with rats are predicting the outcomes of clinical trials with 100% efficiency.

The predictive procedures that have been developed with rats involve the arrangement of a number of conditions that promote intake of alcoholic beverages among rats. The combined effects of those conditions lead rats to take considerable amounts of ethanol daily, enough to produce clear signs of intoxication. The idea is that any agent that is apt to be effective in curbing alcoholics' evidently high motivation to take alcoholic beverages must also reduce intakes of alcoholic beverages among rats that are highly motivated to drink as evidenced by their high daily intake of alcoholic beverages.

Among the conditions that we have arranged with the rats that promoted considerable amounts of intake of ethanol are: (a) Rats are allowed many daily opportunities to voluntarily take alcoholic beverages. (b) The rats are provided with a palatable alcoholic beverage. (c) There is only a two-hour opportunity to drink both water and alcoholic beverages. This procedure produces a state of arousal that seems to promote drinking of alcoholic beverages, but also induces a strong motivation to drink water in order to meet nutritional needs. Research shows that it is not the fact that rats are merely thirsty that they drink more alcoholic beverage when they are slightly deprived of fluids, because they can be provided water before the opportunity to drink alcoholic beverages and they still consume larger amounts of ethanol when they are aroused by the prospects of a daily session of drinking. Also, the drinking of water provides an index of potential debilitating effects of a dose of a drug. A drug that prevents rats from drinking water when they are deprived of water is a drug that is apt to be behaviorally toxic and not of interest from the perspective of selecting drugs as medicines. In other words, the drinking of water provides a similar competing behavior that is highly motivated to occur that can be used to assess the general safety of any agent assessed. (d) The provisioning of fluids occurs during the rats' normal period of sleep. This disruption of normal circadian cycles also seems to promote intake of alcoholic beverages. The combined effects of these arrangements is that rats under this schedule of events develop a strong avidity for alcoholic beverages as long as the beverage is generally palatable.

There are also some other advantages to the procedures we have developed to screen agents for their potential to be medicines for alcohol abuse and alcoholism. The provisioning of a two-hour period to take alcohol allows for the assessment of drugs when the drugs are effective. Such testing does not confound drug-effects and postdrug-effects. The rats maintained under the conditions are generally healthy as indexed by the fact that they gain weight at normal rates.

It is surely the case that excessive intake of alcohol among people is synergistically determined by a number of setting conditions. Any rat model of propensity to drink must also be synergistically determined by a number of setting conditions. It probably does not make much difference what are the exact setting conditions, but it does make a difference as to whether or not there are a number of them that combine to produce the propensity to take alcoholic beverages. Because there are multiple conditions determining the level of drinking does not obviate the possibility that a single drug could have effects in reducing the propensity to drink alcohol. The idea is that the drug is apt to work at a nexus where these multiple influences are integrated.

In summary, the experimental procedures used to come to the conclusion that alpha-2 adrenergic antagonists are effective medicines for alcohol abuse and alcoholism have, in the past, predicted very well the clinical efficacy of drugs in well-controlled clinical trials.

EXPERIMENT 1

This experiment involved dose-response analyses of the effects of two alpha-2 adrenoceptor antagonists on rats' propensities to take an alcoholic beverage. In addition, the effects of an alpha-2 adrenoceptor agonist were assessed. The methods used to establish stable intakes of alcoholic beverage were those that have been used previously as procedures to screen drugs for their efficacy as agents that might mute propensity to take alcoholic beverages.

Method

Subjects

Sixty male, Sprague-Dawley rats were used in these tests. They were purchased from Taconic Farms (Germantown, N.Y.) and they weighed about 175 grams upon their arrival at the laboratory. The rats were housed in individual, standard housing cages and were exposed to twelve hours of artificial light each day. The room where the rats were housed was maintained at 22° C. temperature. After being acclimated to the laboratory for 42 days, the rats were placed on a daily regimen (see above) designed to produce moderately high, but stable, daily intakes of alcoholic beverage. This daily regimen was maintained throughout the study.

The daily regimen consisted of 22 hours of fluid deprivation. Food was available throughout the day. During a specified two-hour period each day, the subjects had unlimited access to fluids. During this two hours, the subjects had a choice of water and a sweetened alcoholic beverage. The alcoholic beverage was 12% (by weight) pure ethanol sweetened with saccharin.

During the first days of the regimen, the subjects consumed little of the alcoholic beverage. As days on the regimen progressed, the subjects increased their consumption until a plateau of 2.5 gram of ethanol per kilogram of bodyweight was reached after about three weeks. After 66 days on the daily regimen, the formal testing procedure was started.

The initial phase of formal testing involved the administration of a placebo to the subjects. During this phase, the average amount of consumption of alcoholic beverage consumed led to the intake of 2.45 grams of pure ethanol per one kilogram of subject bodyweight.

In summary, rats were used that had a well-developed propensity to take alcoholic beverage. After this propensity was established across many days, the effects of drugs were assessed.

Drugs and Alcoholic Beverage Used

The alcoholic beverage employed in these procedures was a sweetened 12% ethanol solution (100 grams of solution contained 12 grams of ethanol and 0.25 grams of saccharin).

The alpha-2 adrenergic agonist used in the test was clonidine hydrochloride (see accompanying list for chemical name) which was purchased from Sigma Chemical Incorporated. This agonist agent was administered in doses of 0.0003, 0.01, 0.03, and 0.1 milligrams per kilogram of subject bodyweight.

The alpha-2 adrenoceptor antagonists employed were (a) methoxyidazoxan (see list for chemical name) purchased from Research Biochemicals Incorporated, which was administered in doses of 0.03, 0.1, 0.3, 1.0, and 3.0 mg/kg and (b) yohimbine hydrochloride purchased from Sigma Chemical Company which was given in doses of 0.001, 0.003, 0.01, 0.1, 1.0, 3.0, and 10.0 mg/kg.

the clonidine and yohimbine were dissolved in distilled water. The methoxyidazoxan was dissolved in a saline solution. The clonidine and yohimbine were subcutaneously injected into the subjects, whereas the methoxyidasoxan was injected intraperitoneally. The placebo for each drug was the carrier for that drug. All drugs and placebos were administered in 1.0 ml volumes per kilogram of bodyweight.

Experimental Procedure

As mentioned, after 66 days on the daily regimen, formal testing procedures were begun. The basic procedure was to first, before a drinking session, give all rats injections of placebos. Then, before the next session, a group of rats were again given placebos and other groups given a dose of one of the agents under study. After an assessment, there were a number of days without injections. Then, the basic procedure was repeated until a full spectrum of doses were sampled.

Just after the day when all rats received injections of placebos, either all 60 of the rats were divided into six groups of ten subjects each, or a portion of the rats were divided into four groups of nine or ten each. Subjects were then randomly assigned to a group with the restrictions that groups for a particular assessment were nearly equal or equal in number and that the mean intakes of alcoholic beverage (in terms of gm/kg of ethanol) were nearly equal. Groups were then randomly assigned for an injection of either another placebo, or a dose of one of the test drugs. After some days without injections, this procedure was repeated until all doses had been assessed. With each round of dosing, there was always one group that received doses of placebos on the second day. For some drugs, a dose was given in more than one round of assessments. As a consequence of the procedure, there were two assessments of the effects of the placebo and two of certain doses of a drug as data of a particular drug's effects were accumulated.

Fluids were presented to the subjects using bottles having ballpoint sipping tubes in order to minimize evaporation and spillage. The differences in weights of the bottles before and after each drinking session (corrected for spillage) were used to measure the amount of intakes. These scores reflecting the amount consumed were later subjected to statistical analyses.

Bodyweights of the subjects were measured about an hour before each daily session. From these basic scores (bodyweights and grams of intake of each kind of fluid), the following additional measure were derived: (a) total fluid taken, (b) amount of ethanol per kilogram of bodyweight (gm/kg) taken, (c) and preference ratios (grams of alcoholic beverage consumed divided by total fluid intake).

Because of the possibility of the history of a subject interacting with a particular drug, there were similar tests conducted with a different set of rats who had a similar history of being on the daily regimen but a different history or no history of administration of the drugs in question. These additional tests were usually with only one selected drug dose. The results from these additional tests verify the results with the first assessments and indicate that history of subjects was not a factor in determining outcomes of the test. The results of these tests are not discussed further.

Three indices of a drug effects, across doses, adequately characterize the results (gm/kg of pure ethanol taken, grams of water taken, and preference ratios), since some of the scores are highly correlated (e.g., grams of ethanol taken and gm/kg of ethanol taken). Student t-tests for independent and dependent measures were used to assess the statistical significance of a particular drug dose's effect.

Drug dosages were based upon published behavioral studies with the agents employed (see, e.g., "Interactions of an Alpha-2 Adrenoceptor Antagonist With Medtomidine and With Ethanol in a Holeboard Test," 28 *Neuropharmacology*, 275–281, 1989, Durcan et al.; and "Assessment of the Functional Role of Brain Adrenergic Neurons: Chronic Effects of Phenylethanolamine N-Methyltransferase Inhibitors and Alpha Adrenergic Receptor Antagonists on Brain Norepinephrine Metabolism," 230 (3), *J. Pharmacology Exp. Ther.*, 577–586, 1984, Stolk et al.) and upon the initial assessments with a particular drug. When the first set of doses included a dose that was debilitating (i.e., dramatically reduced intake of water), then the next round of dosing included lower doses. When doses used at first had no discernible effect, a second assessment of the drug was undertaken with a set of higher doses. As a consequence of this procedure, a full range of doses were sampled from those having no effects to those, in some cases, that are of little interest because they approach toxic levels of dosing. Further, as a consequence of the procedure, an optimal dosage was discerned for the antagonists, i.e., a dose that produced marked reductions in intake of alcoholic beverage without concurrently producing market reductions in intake of water.

Since the experiment arranged that the highest dose of a drug was also a dose that produced some effects and often was so high that it dramatically reduced intake of water, the question of interest is whether there are levels of drug dosage which produce a statistically significant decrease in alcohol consumption while producing moderate or no change in the intake of water (a reliable sign of a lack of adverse effects). This ability to maintain overall fluid intake while lowering alcohol beverage intake indicates that the drug does not produce general malaise which might affect the subject's ability and interest in attending to basic needs. The lowering of preference ratios in such cases is most indicative of a drug's effectiveness in curbing alcohol preference, provided that the drug does not reduce intakes of water dramatically.

Results and Discussion

The data for clonidine, the agonist, indicate that clonidine had little effect on increasing intakes of alcoholic beverages, with the exception of the dose of 0.003 mg/kg which produced a slight increase in consumption. This same dose, however, increased intakes of water a slight amount also. Doses of 0.01, 0.03, and 0.1 of clonidine produced such radical reductions in intake of water that they are of little interest. In general, the conclusion from the tests with clonidine was that clonidine had little specific effect on intake of alcoholic beverage.

Figure 1B:
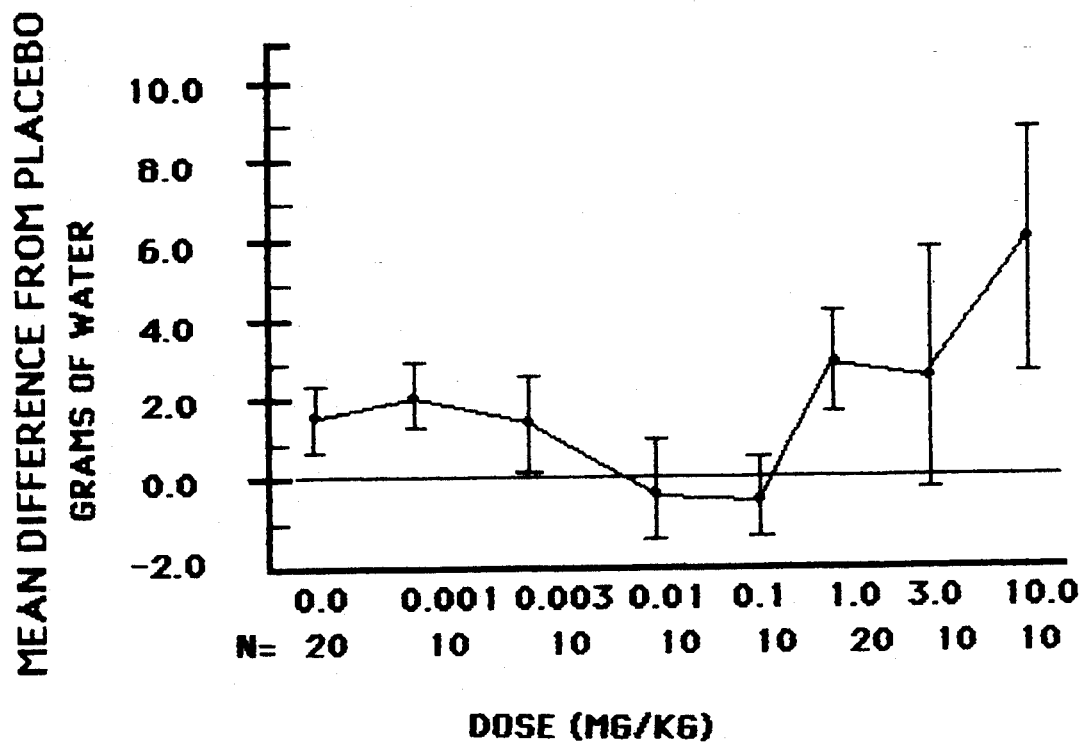
Figure 1C:
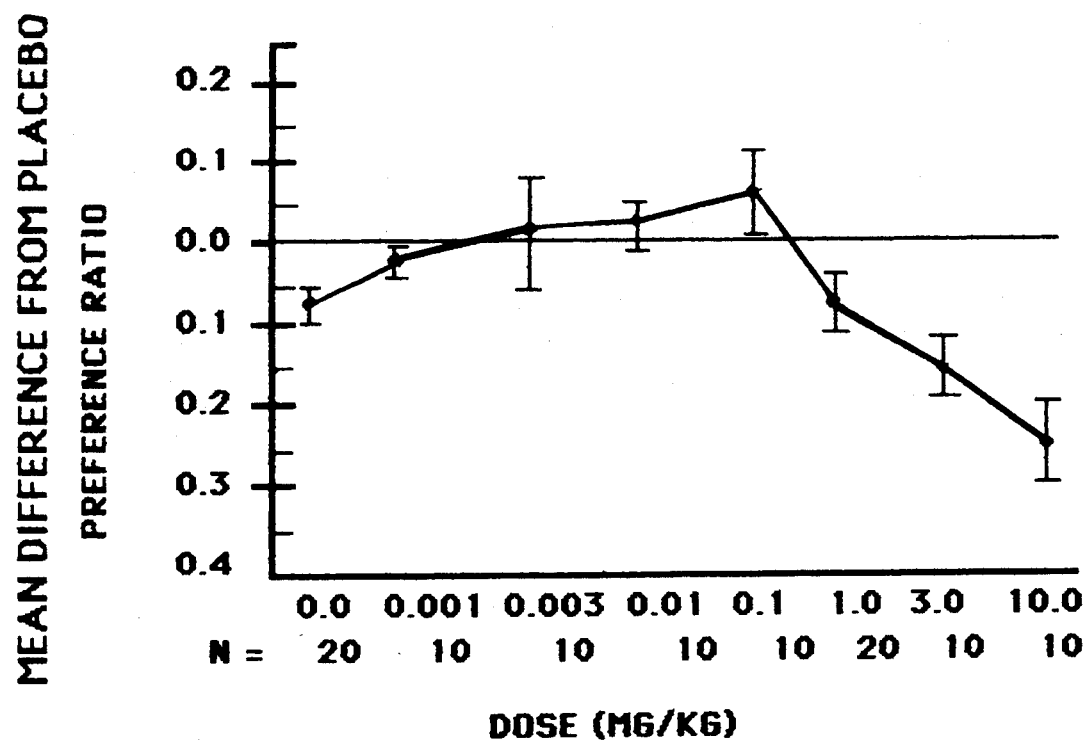
Figure 2A:
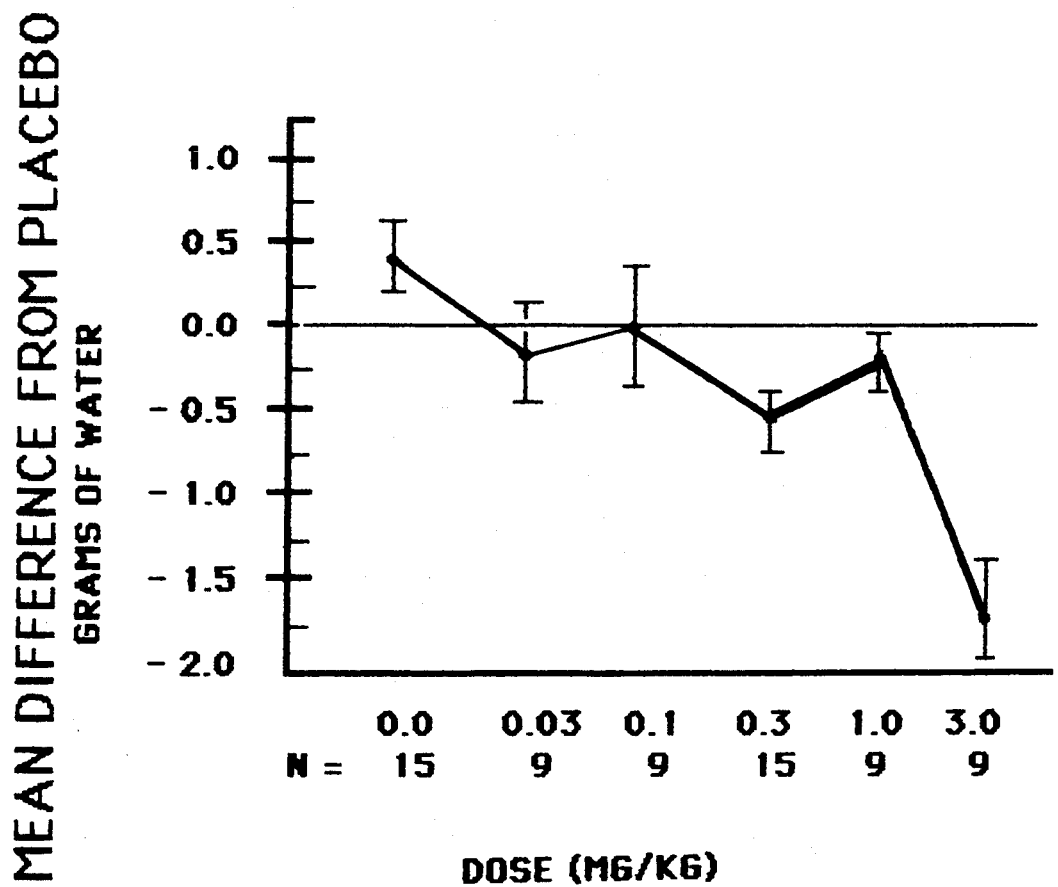
Figure 2B:
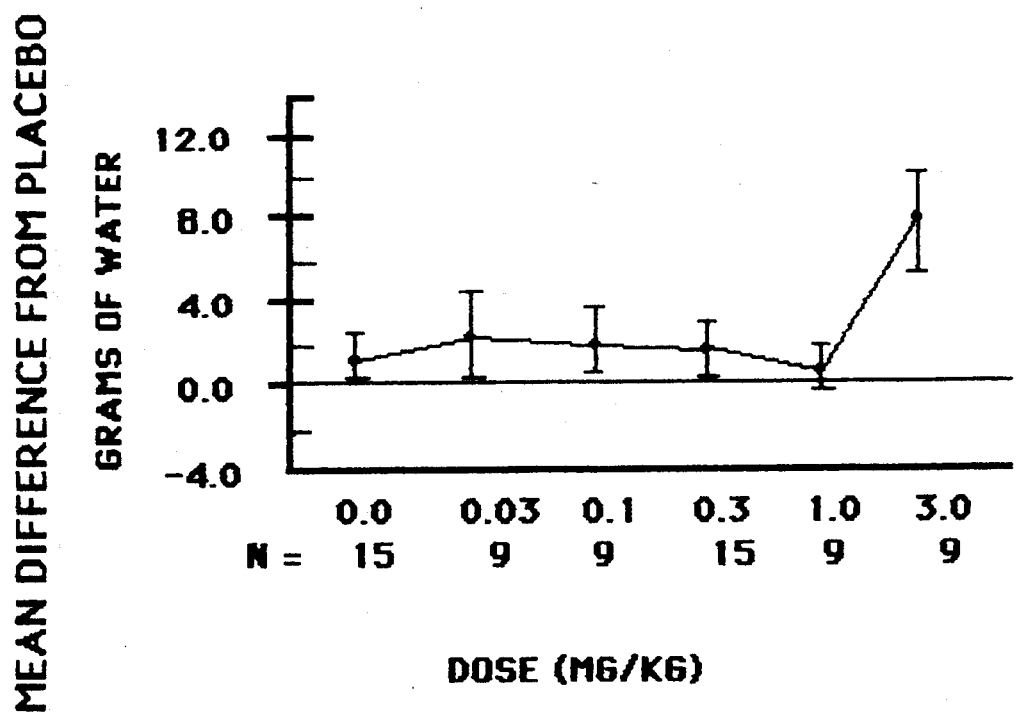
Figure 2C:
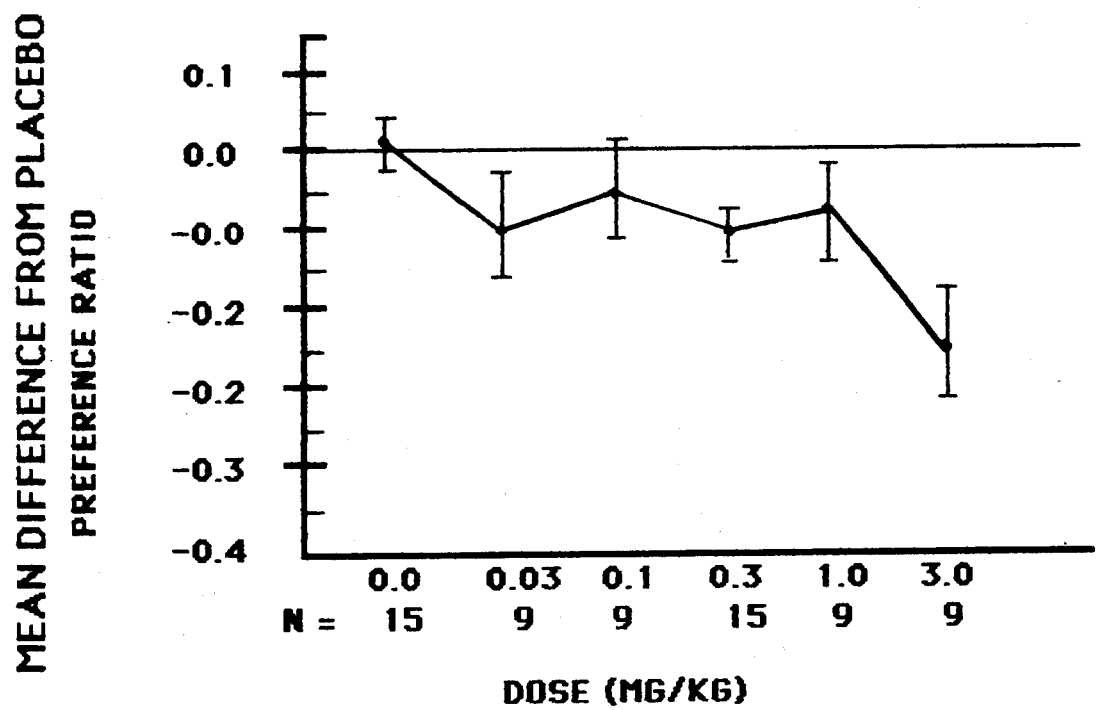

The accompanying FIGS. 1-2 summarize the effects of the two antagonists on subjects' intakes. For each drug, there was little shift or decrease in alcohol consumption when the smallest doses of each drug is employed.

Yohimbine (see FIG. 1) produced no marked effects on intake of water or alcoholic beverage until doses of 1.0, 3.0, and 10.0 mg/kg were given. At these doses, the drug decreased intakes of alcoholic beverage (hence gm/kg of pure ethanol), increased intake of water, and decreased preference ratios. There is a marked and statistically significant reduction in consumption of alcohol with doses of Yohimbine of 3.0 and 10.0 mg/kg. At these doses, Yohimbine tended to increase intakes of water and, therefore, the rats took their usual total amount of fluid. This ability to maintain adequate fluid intake indicates that Yohimbine's effects are specific to alcoholic beverages.

The data displayed in FIG. 2 summarizes the effects of methoxyidasoxan. Dosage levels of 0.3, 1.0, and 3.0 mg/kg decrease consumption of alcohol. Only the dosage of 3.0 mg/kg increased the subjects' consumption of water markedly to compensate for the fluid usually acquired by taking alcoholic beverage. All dosages greater than 0.03 mg/kg produced a decrease in the preference ratio.

These are the first data to show that administration of specific alpha-2 adrenoceptor antagonists reduces avidity for alcoholic beverages. Furthermore, the doses that were effective in reducing intakes of alcohol do not reduce intakes of water when opportunities to take both were presented concurrently. The fact that these agents reduce propensity to take an alcoholic beverage when there is a strong motivation to do so (as evidenced by intakes under placebo), but do not interfere with ability to meet nutritional needs, indicates that alpha-2 adrenoceptor antagonists are a reasonable pharmacological intervention for treating alcohol abuse and alcoholism and related disorders characterized by a tendency to take excessive amounts of alcoholic beverage.

EXPERIMENT 2

It is interesting to show that alpha-2 adrenoceptor antagonists selectively, and dose-relatedly, decrease rats' propensity to take alcoholic beverages (Experiment 1). Such data indicate that this kind of agent will be an effective pharmacological adjunct to other treatments for alcohol abuse and alcoholism. The case, however, that any one of a number of this kind of agent might be a medicine for treating alcoholism would be strengthened if other members of the class produced similar effects. Here, we present sthe results of testing three other members of the class using an arbitrarily selected dose of each.

Method

The same kind of subjects as used in Experiment 1 were used in this experiment. Similar procedures were used, i.e., rats were given daily two-hour opportunities to take both water and alcoholic beverage (12% sweetened alcoholic beverage) daily following twenty-two hours of deprivation of water. Food was always available. After stabilization of intakes and many daily opportunities to take alcoholic beverage, the effects of drugs were assessed by giving injections of drugs before an opportunity to drink.

The sixty rats of these procedures had been on the daily regimen for seventy-four days prior to this testing, i.e., they had a daily opportunity to voluntarily take alcoholic beverage for seventy-four days before these procedures began. They were taking, on average, over 2.0 grams of pure ethanol per kilogram during each daily session just prior to the trials of this experiment. This is a sufficient amount of ethanol to produce signs of intoxication (such as slowed righting reflexes). On the day before injections of drugs, all rats received injections of placebos, the carrier of the drugs, physiological saline. Data from this day of injections of placebos were used to designate four groups. Rats were randomly assigned to groups except for the provision that each group had fifteen rats and that each group was arranged to have nearly equal intakes of ethanol.

On the day following injections with placebos, one group again received injections of placebo (a control group), another group received injections of idazoxan, another received injections of efaroxan, while another received injections of rauwolscine. The assignment of which group received which drug was random.

Idasoxan, efaroxan and rauwolscine (see chemical names in the list) were each given in a dose of 3.0 mg/kg. Injections were given fifteen minutes before the opportunity to drink both water and alcoholic beverage. Volume of all injections were 1.0 ml/kg.

Measures of intake were similar to those used in Experiment 1. The resulting data were handled similarly to that of Experiment 1.

Results and Discussion

Figure 3:
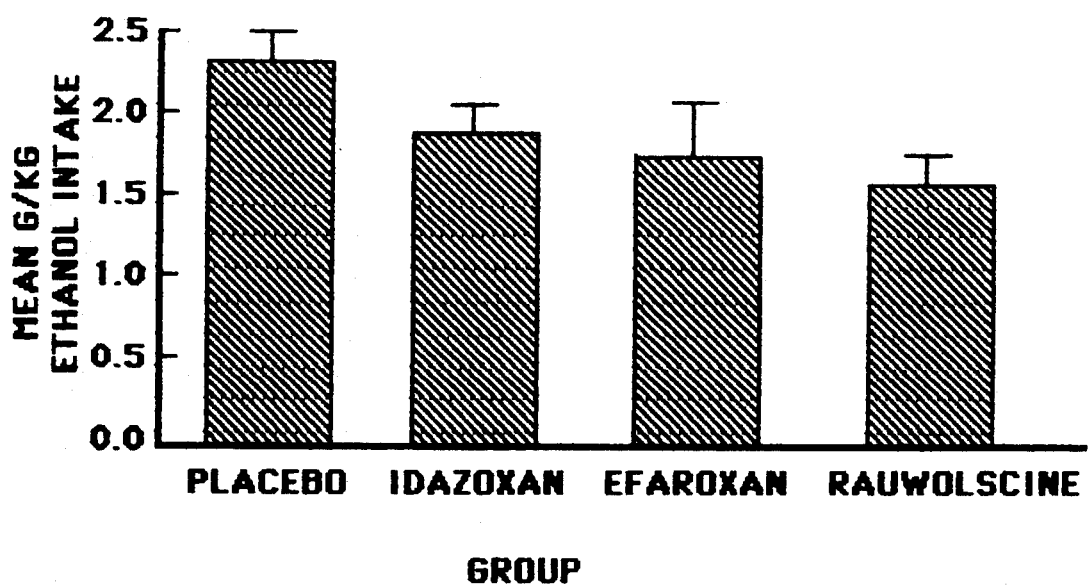
FIG. 3 depicts the mean grams of pure ethanol per kilograms of bodyweight, taken by each group during 2 hours. The lines above the bars depict standard errors of the mean. Placebo refers to the group receiving only injections of the carrier of drugs. The other designations refer to a dose of one of three different alpha-2 adrenergic antagonists given before rats had their daily opportunity to take alcoholic beverage.

The data are summarized in FIG. 3. Note that each agent significantly reduced intake of ethanol. The doses used in these assessments were selected rather arbitrarily. It is reasonable to suppose that with larger doses a larger reduction in intake of alcoholic beverage is apt to be achieved. It also should be noted that none of the alpha-2 adrenergic antagonists produced reductions in intake of water which indicates that the reduction in intakes of alcoholic beverage are not apt to be due to the production of a malaise or a debility that would prevent rats from drinking or meeting their nutritional needs.

These data provide strong support for the idea that any one of the alpha-2 adrenoceptor antagonists might be effective in reducing propensity to take alcoholic beverages, and hence, be a reasonable medicine for treating alcohol abuse and alcoholism.

EXPERIMENT 3

A weakness of the data collected in Experiment 1, germane to concluding that alpha-2 adrenergic systems are saliently involved in propensity to take large amounts of alcoholic beverages, is that the agonist clonidine did not increase intakes. It would be expected, if alpha-2 adrenergic systems are salient to excessive intake of alcoholic beverages, that the agonist would increase intakes and that the antagonists would decrease intakes. Antagonists clearly reduce intakes, but the agonist tested, clonidine, produced only a marginal increase in intakes. Previous results indicate that there are a number of setting conditions that potentiate rats' intake of alcohol, including some that were used in the procedures of Experiments 1 and 2 such as providing palatable alcoholic beverages and providing rats with many daily opportunities to take alcohol. There is another setting condition that has been shown to increase rats' intake of alcoholic beverage, the injection of moderate doses of morphine.

The idea underlying this experiment is that clonidine might potentiate intakes when there are more setting conditions extant. If clonidine would interact with a small dose of morphine to produce more intake than either one alone, in a situation where rats were already taking considerable amounts of alcohol, then there would be additional support for the idea that alpha-2 adrenergic systems were salient to propensity to take excessive amounts of alcoholic beverage. Here, we show that the effects of small doses of clonidine combined with the effects of very small, generally ineffective, doses of morphine produces a marked propensity to consume large amounts of alcohol (over 2.5 grams of ethanol per kilogram of bodyweight).

Method

The methods used in this experiment are similar to those used in the previous experiments. The sixty rats had been on the daily regimen previously described for sixty-one days. On the next day, all were given injections of placebos (two injections). Using the data of this day of placebo-injections, the rats were assigned to one of four groups, fifteen rats a group. The groups were arranged so that each group consumed nearly equal amounts of alcohol.

On the day following injections of placebos and before rats' opportunity to drink both alcoholic beverage and water, one group again received placebos. Another group received a dose of clonidine (0.003 mg/kg, 15 min before opportunity to drink) and an injection of placebo. Another group received a dose of morphine (0.05 mg/kg, 10 min before the opportunity) and an injection of placebo. This dose of morphine is not sufficiently large to produce significant increases in intakes of alcoholic beverage. This dose of morphine is, however, sufficiently large to produce some effects in brain that are thought to be important with respect to propensity to take alcoholic beverages. A fourth group received the dose of clonidine and the dose of morphine given to the other groups.

The resulting data were handled as the data of the previous experiments. The data associated with grams of pure ethanol taken per kilogram of bodyweight is an adequate summary of results.

Results and Discussion

Figure 4:
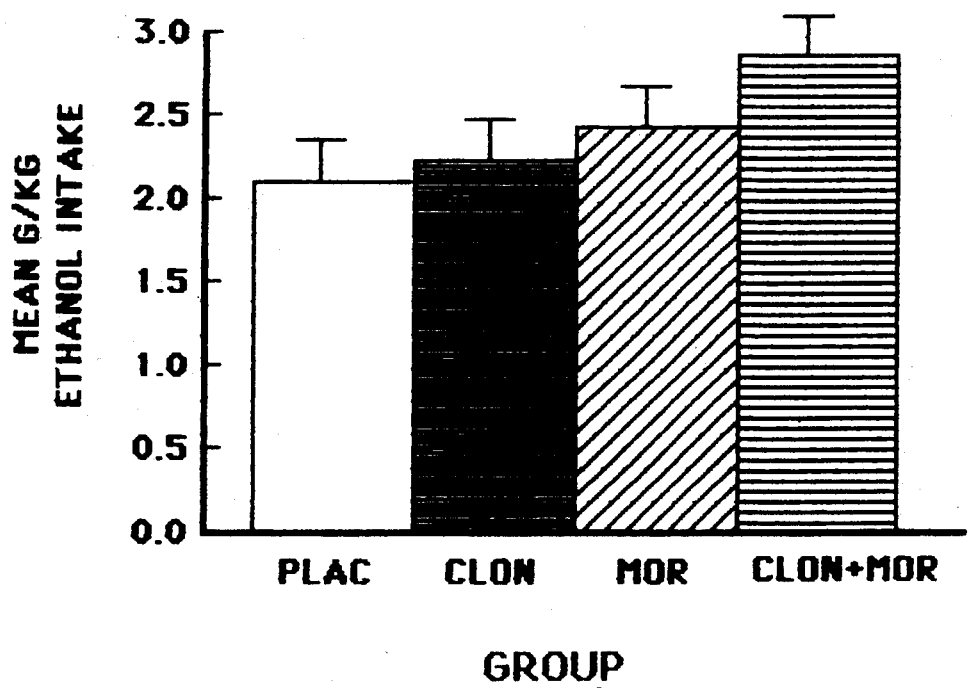
FIG. 4 depicts means grams of pure ethanol taken per kilogram of bodyweight for each group. One group only received placebos. Another group received a small dose of morphine and a placebo. Another group received doses of clonidine and placebo. Another group received both doses of morphine and doses of clonidine. Notice that the doses of clonidine potentiated the effects of morphine, an agent known, in larger doses, to produce some potentiation of propensity to take alcoholic beverages.

The results are summarized in the accompanying Figure. Notice that this very small dose of morphine produced almost no increment in intake of ethanol. Notice in FIG. 4 that clonidine also produced only marginal increases in intake of alcohol as it did with the rate of Experiment 1. The combined effects of morphine and clonidine, however, produced a marked increase in intake of alcohol.

These data support that an alpha-2 agonist can potentiate intake of alcoholic beverages. These data, therefore, strengthen the idea that alpha-2 adrenergic systems are salient to propensity to take large amounts of alcoholic beverages. These data, also, provide support for the idea that alpha-2 adrenoceptor antagonists would be effective medicines to curb propensity to take large amounts of alcoholic beverages.

EXPERIMENT 4

Alcohol abuse and alcoholism are characterized by periods of excessive amounts of intake of alcoholic beverages, followed by periods of abstinence (usually, today, these periods of abstinence involve some form of treatment involving withdrawing in a hospital setting and receiving counseling), which, in turn, are followed by periods of relapse into excessive drinking with intakes of alcoholic beverages being as great or greater than those that preceded the period of abstinence (treatment). This cycle of drinking, abstinence, and relapse continues for many alcoholics (but surely not all) until their health becomes so bad that they suffer serious disease and death.

A beneficial medicine for alcohol abuse and alcoholism would decrease the propensity to take alcoholic beverages following a period of abstinence. A beneficial medicine need not totally reduce propensity to take alcoholic beverages, but merely mute that propensity. A drug that completely blocked intake of all alcoholic beverages, in fact, is apt to be so toxic that it would be of little value (for example, such an agent might reduce propensity to take adequate nutrients). What is needed is a drug that decreases the motivation to consume large amounts of alcoholic beverages so that the alcoholic can bring to bear more easily other motivations to refrain from relapsing into extended periods of excessive drinking of alcoholic beverages.

In this experiment, rats that had many days to consume alcoholic beverages under conditions that potentiate drinking did, indeed, take considerable amounts of beverage. They were then deprived of the opportunity to consume alcoholic beverages for a period. Then, they were again given the opportunity to take alcohol daily while some of them were under the influence of an alpha-2 adrenoceptor antagonist. The antagonist reduced rats' intakes, compared to those receiving placebos, thereby supporting the idea that alpha-2 antagonists would be an effective medicine for treating alcohol abuse and alcoholism.

Method

The thirty-five subjects of this experiment were the same type of subjects used in the previous experiments. These rats were treated very similarly to those of the previous experiments, except for the procedures specific to this test. The alcoholic beverage (12% ethanol) for roughly half of the subjects was sweetened with sucrose and, for half, with saccharin. The rats were on the daily regimen for over four months. Then, the subjects were taken off of the daily schedule and given no alcoholic beverages for nine days (of course, they were provided adequate food and water during the period of abstinence). The day before they were taken off the schedule, the subjects were taking a mean of 2.2 gm of pure ethanol per kilogram of bodyweight.

At the end of the period of abstinence (no alcoholic beverages), one half of the subjects were given a 3.0 mg/kg dose of methoxyidazoxan, subcutaneously, fifteen minutes before their usual daily opportunity to take alcoholic beverage and water for two hours a day. The other half received placebos before their opportunity to drink.

For twelve consecutive days, rats received their injections before each daily opportunity to drink. Then, injections were stopped, but the rats continued on the daily regimen while their intakes were monitored for an additional eight days.

In summary, this was a test to see whether or not a dose of methoxyidasoxan, a specific alpha-2 adrenoceptor antagonist, retarded the development of the propensity to take large amounts of alcoholic beverages after a period of abstinence. If the drug did retard the development of a propensity to take alcoholic beverages, it would be concluded that methoxyidazoxan (and similar drugs) would be an effective medicine to prevent relapse into heavy drinking which is the characteristic event in a history of alcoholism.

Results and Discussion

Figure 5:
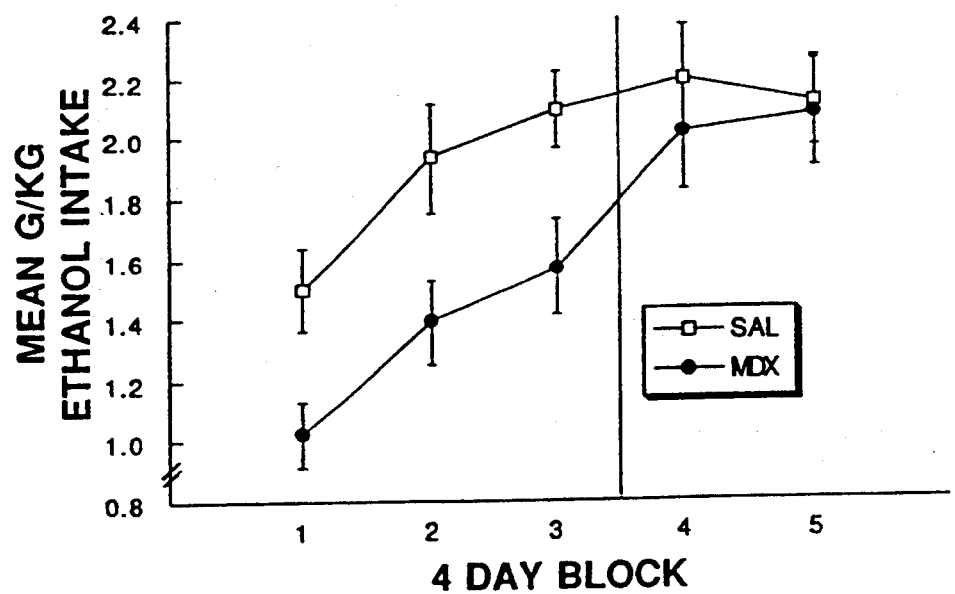
FIG. 5 depicts the data presented are mean intakes across four-day blocks for two groups, one of which received methoxyidazoxan and one of which received placebos for twelve days (3 blocks). These intakes of ethanol are after a period when rate had no opportunity to take alcoholic beverage. The data for Blocks 4 and 5 are after injections were stopped.

The results of this test are provided in FIG. 5. The values to the left of the figure are means (plus or minus standard errors of the mean) of four-day blocks of days while rats were either under the influence of placebos or methoxyidazoxan (data points to the left of the line). Since there were no reliable differences associated with the kind of alcoholic beverage, the values in FIG. 5 do not reflect this distinction. The data to the right of the line in FIG. 5 reflect the two four-day blocks when injections were no longer given.

The animals under the condition of placebo rather quickly resumed high levels of intakes when presented a daily opportunity to voluntarily consume one of two kinds of alcoholic beverage. Notice that animals under the influence of an alpha-2 adrenergic antagonist had a reduced propensity to take alcoholic beverage throughout the period of drug administration. These data provide further support for the idea that alpha-2 adrenoceptor antagonists would be useful medicines for treating alcohol abuse and alcoholism.

Both groups of rats took adequate amounts of water during the twelve-day period and there was no statistically significant difference between amounts of water taken by the groups. Statistical analyses indicate that the group under the influence of drug took significantly less alcohol throughout the period when the drug was given.

These tests involved two kinds of alcoholic beverage, the kind used in Experiments 1-3 and one sweetened with sucrose. The drug worked equally well with both. In similar studies, it was found that when an agent was effective in reducing intakes of one kind of alcoholic beverage that it was effective in reducing intakes of other kinds (we have even tested beverages such as commercially available beer). The alcoholic beverages used in these tests are evidently palatable for rats (they take very large amounts of these beverages when they contain no alcohol and they take sufficient amounts of these beverages when they contain ethanol to show clear signs of intoxication). It is concluded, therefore, that alpha-2 adrenergic antagonists would be effective across the range of available alcoholic beverages.

LIST OF GENERIC NAMES AND CHEMICAL NAMES OF COMPOUNDS USED IN THE TEXT AND OTHER ALPHA-2 ADRENERGIC ANTAGONISTS

ALPHA-2-ADRENOCEPTOR AGONIST USED

Clonidine: 2-(2,6-dichloroalanine)-2-imidazoline

ALPHA-2-ADRENOCEPTOR ANTAGONISTS USED

Efatoxan HCl: 2-(2-ethyl-2, 3-dihydro-2-benzofuranyl)-4, 5-dihybro-1E-imidazole hydrochloride Idazoxan BCl: ($\pm$)-2-(1,4-benzodioxan-2-yl)-2-imidazoline hydrochloride LY78335: 2,3-dichloro-alpha-methylbenzylamine Methoxyidazoxan HCl: HCl-2-(2-(2-methoxy-1,4-benzodioxanyl)) 2-imidazoline hydrochloride Rauwolscine HCl: 17 alpha-hydroxy-20 alpha-yohimban-16 beta carboxylic acid methyl ester hydrochloride Yohimbine HCl: 17-hydroxyyohimban-6-carboxylic acid methyl ester hydrochloride

EXAMPLES OF OTHER ALPHA-2-ADRENOCEPTOR ANTAGONISTS

CH-38083: (7,8-(methylenedioxi)-14-alpha-hydroxyalloberbane hydrochloride

Fluparoxan BCl: trans-($\pm$)-5-fluoro-2,3,3a,9a-tetrahydro-1H(1,4) -benzodioxino-92,3-c)pyrrole hydrochloride LY134046: 8,9-dichloro-2,3,4,5-tetrahydro-1H-2-benzodiazepine Midaglozole Dihydrochloride Sesquihydrate (DG-5128): 2-(2-(4,5-dihydro-1H-imidazol-2-y))-phenylethyl)-pyridine dihydrochloride sesquihydrate RS-21361: 2-(1-ethyl-2-imidazolyl methyl)-1,4-benzodioxan RS-49640: 2-(1-methyl-2-imidazolyl methyl)-1,4-benzodioxan RS-84663: 2-(2-imidazolyl methyl)-1,4-benzodioxan A structural hydrid between Rauwolscine and WT26703;

(8a-alpha, 12a-alpha, 13a-alpha)-5,8,8a,9,10,11,12,12a, 13,13a, decahydro-3-methoxy-12-(methylsulfonyl)-6H-isouino(2,1-g)(1,6) naphthyridine These alpha-2-adrenergic antagonists are known to those skilled in the pharmaceutical art and their preparation is described in the art, as they are commercially available.

SUMMARY OF EXPERIMENTS AND CONCLUSION

The data of these experiments show that alpha-2 adrenergic antagonists significantly reduce intakes of alcoholic beverages. This reduction occurs at doses that do not decrease intake of water, therefore, confirming the novel invention that alpha-2-adrenergic antagonists are effective medicines for treating alcohol abuse and alcoholism.

Therefore, what is claimed is:

1. A method for decreasing appetite for alcohol in humans which comprises administering to said humans an effective dosage of methoxyidazoxan.

2. The method of claim 1 wherein said effective dosage is administered orally.

3. The method of claim 1 wherein said effective dosage is administered by subcutaneous injection.

4. The method of claim 1 wherein said effective dosage is administered by intramuscular injection.

5. A method for decreasing appetite for alcohol in humans which comprises administering to said humans an effective dosage of RS-21361.

6. The method of claim 5 wherein said effective dosage is administered orally.

7. The method of claim 5 wherein said effective dosage is administered by subcutaneous injection.

8. The method of claim 5 wherein said effective dosage is administered by intramuscular injection.

9. A method for decreasing appetite for alcohol in humans which comprises administering to said humans an effective dosage of an alpha-2-adrenergic antagonist selected from the group consisting of RS-49640 and RS-84663.

10. The method of claim 9 wherein said effective dosage is administered orally.

11. The method of claim 9 wherein said effective dosage is administered by subcutaneous injection.

12. The method of claim 9 wherein said effective dosage is administered by intramuscular injection.

* * * * *